US008163300B2

(12) United States Patent
Han et al.

(10) Patent No.: US 8,163,300 B2
(45) Date of Patent: Apr. 24, 2012

(54) METHOD FOR ENHANCING DISPERSION OF INORGANIC COMPOUNDS USING SILICONE-CONTAINING ESTERS AND COMPOSITIONS FORMED THEREFROM

(75) Inventors: Wenning Wang Han, Lawrenceville, NJ (US); James Zielinski, Somerset, NJ (US); Bernie J. Pafford, Berkeley Heights, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 657 days.

(21) Appl. No.: 12/044,718

(22) Filed: Mar. 7, 2008

(65) Prior Publication Data

US 2009/0226385 A1    Sep. 10, 2009

(51) Int. Cl.
| | |
|---|---|
| A61K 8/02 | (2006.01) |
| A61K 8/00 | (2006.01) |
| A61K 8/18 | (2006.01) |
| A61K 31/01 | (2006.01) |
| A61Q 15/00 | (2006.01) |
| A61Q 17/04 | (2006.01) |
| A01N 27/00 | (2006.01) |
| C07F 7/00 | (2006.01) |

(52) U.S. Cl. .......... 424/401; 424/59; 424/65; 514/770; 556/439

(58) Field of Classification Search .............. None
See application file for complete search history.

(56) References Cited

U.S. PATENT DOCUMENTS

| | | | |
|---|---|---|---|
| 4,725,658 A * | 2/1988 | Thayer et al. ............... | 528/15 |
| 4,900,542 A | 2/1990 | Parrotta, Jr. et al. | |
| 6,447,791 B2 * | 9/2002 | Kowalik et al. ............. | 424/401 |
| 2008/0108842 A1 * | 5/2008 | Pafford et al. .............. | 556/439 |

FOREIGN PATENT DOCUMENTS

| | | |
|---|---|---|
| EP | 1 632 213 | 3/2006 |
| WO | WO 92/05767 | 4/1992 |
| WO | WO 97/06777 | 2/1997 |
| WO | 2006/066227 | 6/2006 |
| WO | 2006/127883 | 11/2006 |
| WO | 2007/035315 | 3/2007 |

OTHER PUBLICATIONS

Anonymous, "*Shin-Etsu Silicones for Personal Care*," [online] Mar. 2004 [retrieved on May 20, 2009]. Retrieved from the Internet:<URL: http://web.archive.org/web/20060516090726/http://www.shinetsusilicones.com/KP_3.pdf, Product Brochure, KP Series KP-541.543.545.561P.562P.575, Mar. 2004, pp. 1-7.

(Continued)

*Primary Examiner* — Carlos Azpuru
*Assistant Examiner* — David Browe

(57) ABSTRACT

A cosmetic composition comprising: (a) an aqueous and/or oil phase comprising: (i) water, and (ii) at least one cosmetically active ingredient; (b) a coupling agent; and (c) an oil phase comprising: (i) an isoparaffin solvent, and (ii) a silicone-containing solvent having the formula:

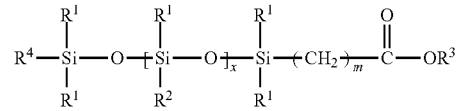

13 Claims, 3 Drawing Sheets

OTHER PUBLICATIONS

Shaath, N.A., "*SPF Boosters & Photostability of Ultraviolet Filters*," [online] Oct. 2007, Happi Magazine, vol. 2007, No. 10, [retrieved on May 20, 2009]. Retrieved from the Internet:<URL: http://www.happi.com/articles/2007/10/spf-boosters-photostability-of-ultraviolet-filt.

Van Reeth, I. et al. "*Silicones Bring Multifunctional Performance to Sun Care*," Oct. 2006, Cosmetics & Toiletries Magazine, vol. 121, No. 10, pp. 41-54.

Rachid Zniber, et al, "*Columnar Mesophase from a New Hybrid Siloxane-Triphenylene*", Journal of Materials Chemistry, vol. 12, No. 8, Jul. 26, 2002, pp. 2208-2213.

Richard A. Evans et al., "*The Generic Enhancement of Photochromic Dye Switching Speeds in a Rigid Polymer Matrix*", Nature Materials, vol. 4, No. 3, Mar. 1, 2005, pp. 249-253.

* cited by examiner

Fig. 2

Brookfield Viscosity at Ambient T*

| Z-Cote HP-1 added, gram | PureSyn 6 | PureSyn 3E20 | MCP 2262 | Exxon Di-10 | Exxon Di-45 | Exxon Di-100 | Exxon D2 | Exxon D10 |
|---|---|---|---|---|---|---|---|---|
| 15 | 90 | 480 | 880 | 140 | 340 | 460 | 130 | 150 |
| 30 | 3600 | 4500 | 5400 | 1620 | 1350 | 1240 | 160 | 360 |
| 45 | 9000 | 13300 | 16000 | 4000 | 4200 | 3900 | 900 | 1260 |
| 60 | 18000 | | | 8400 | 8000 | 8500 | 3100 | 4650 |
| 75 | | | | 16000 | 13000 | 15400 | 9000 | 10400 |
| 90 | | | | | | | 12800 | |

*Z-Cote HP-1 added to 75 grams of test fluid in 15 gram increments.
Sample homogenized for 15 min at 9000 RPM on LR4T Silverston Homogenizer.
Brookfield Viscosity at ambient T was measured after 2 min.
*Experiment by Cosmetech

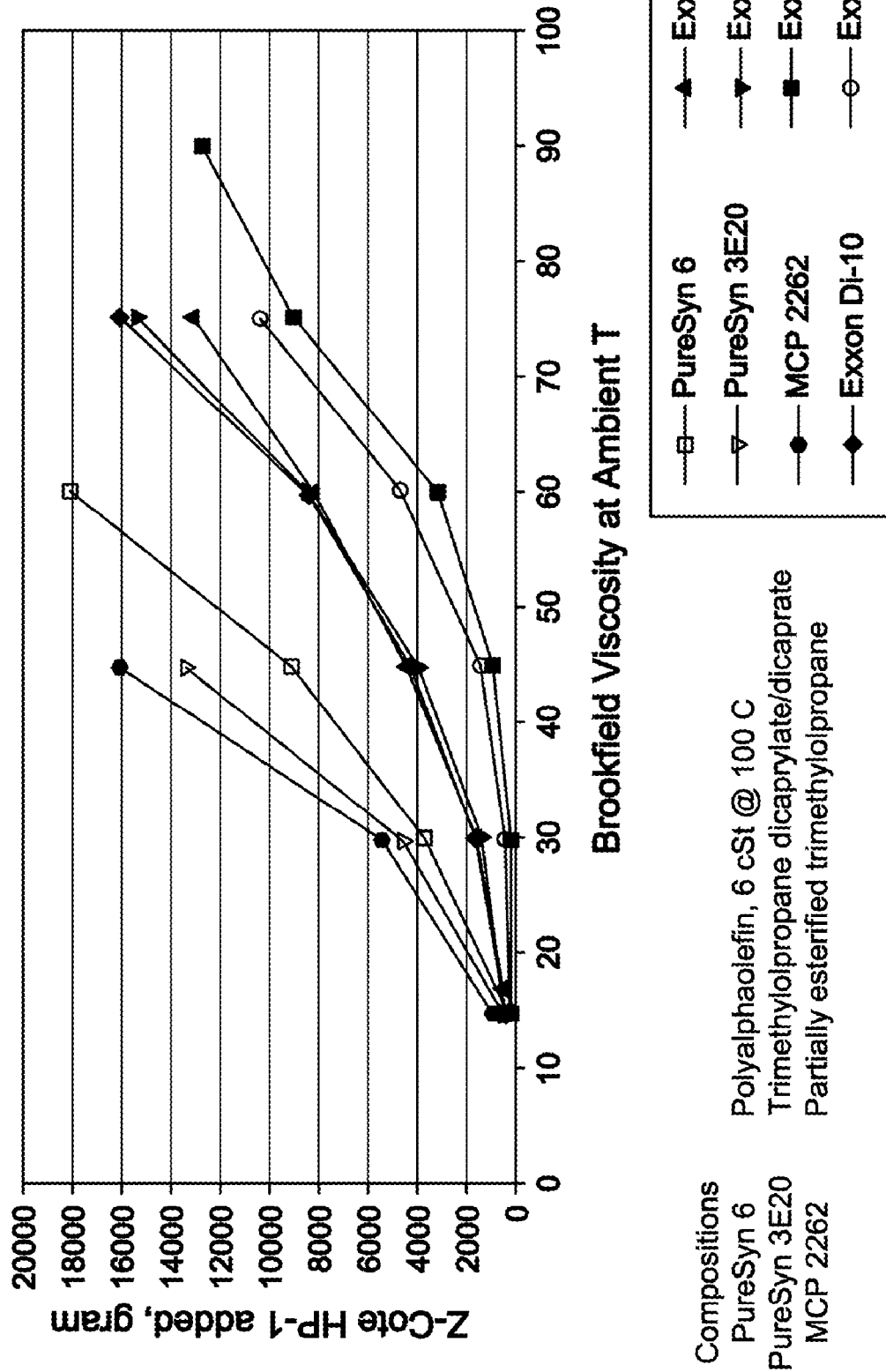

METHOD FOR ENHANCING DISPERSION OF INORGANIC COMPOUNDS USING SILICONE-CONTAINING ESTERS AND COMPOSITIONS FORMED THEREFROM

FIELD OF THE INVENTION

The present disclosure relates to dispersion of inorganic compounds, such as zinc oxide compounds, using silicone based fluids having silicon groups and organic groups linked through ester linkages. The silicone based fluids are preferably formed from the reaction of vinyl-terminated carboxylic acid esters of partially esterified esters with hydride containing polysiloxanes. The vinyl-terminated carboxylic acid esters of partially esterified esters are formed from the reaction of multifunctional alcohols with vinyl-terminated carboxylic acids. Preferably, the resultant formulation is useful in sunscreen, antiperspirant/deodorant and facial makeup formulations at lower concentrations because of their superior dispersing properties.

BACKGROUND OF THE INVENTION

Antiperspirant and deodorant products are well-known in the cosmetic art. They are generally used by rubbing an area of the body such as the underarm to apply a layer of the composition to the skin which reduces odor and/or perspiration. It is desirable that such products have aesthetic characteristics of non-crumbling, smoothness, non-oiliness and non-tackiness. Clarity of such products is a long-sought desirable aesthetic characteristic. Another desirable characteristic is that no readily visible residue as, e.g., a white layer, be left on the skin after the deodorant or antiperspirant is applied.

Antiperspirant and deodorant products have appeared in the marketplace in various dosage forms, such as sticks, gels, roll-ons, aerosols and creams. Generally, these dosage forms include a solution of the active ingredient in a suitable solvent, a suspension of the active ingredient in a non-solvent, or a multiphase dispersion or emulsion in which a solution of the active ingredient is dispersed in some continuous phase or in which the solubilized active ingredient constitutes the continuous phase.

The stick form has become the dominant antiperspirant dosage form in the United States market, constituting more than 50% of total antiperspirant sales, and is popular to varying degrees globally. Cosmetically acceptable antiperspirant sticks typically consist of a suspension of spray-dried active antiperspirant material in vehicles such as cyclomethicone, with a waxy substance such as stearyl alcohol, alone or in combination with castor wax, gelling or thickening the suspension sufficiently to create a suitable stick.

The stick form can be distinguished from a gel or a paste in that in a stick, the formulated product can maintain its shape for extended time periods outside the package, the product not losing its shape significantly (allowing for some shrinkage due to solvent evaporation).

The hard stick dosage form, although widely accepted by the consumer, suffers from leaving a white residue on skin after application, and can cause staining of fabric, which is considered to be undesirable, particularly by female consumers. The gel dosage form can be formulated to reduce and/or eliminate the white residue.

One such clear gel antiperspirant is set forth in International Patent Application No. WO 92/05767, published on Apr. 16, 1992 (The Gillette Company), which is incorporated herein by reference. This patent application pertains generally to a clear gel-type cosmetic product which includes an emulsion with an oil phase and a water phase that includes an incorporated active ingredient. The oil phase preferably makes up about 10 to 25% of the product and includes an emulsifier which when properly mixed with the water phase components yields a water-in-oil emulsion. The oil phase is typically a blend of liquids and includes a polyorganosiloxane (e.g., dimethicone) and a silicone emulsifying agent. A particularly suitable emulsifying agent is a polyether substituted silicone of cyclomethicone and dimethicone copolyol. This emulsifier is useful for preparing stable water-in-oil silicone emulsions where silicone makes up a large portion of the oil phase, and is a dispersion of a silicone surfactant (i.e., dimethicone copolyol), i.e., 10% silicone surfactant in cyclomethicone (i.e., a silicone solvent). The water phase includes one or more polar species such as water, propylene glycol, sorbitol and ethanol. The water phase includes, in solution, a deodorant and/or antiperspirant active ingredient such a triclosan, benzethonium chloride and/or an astringent salt of aluminum or zirconium, such as aluminum chlorohydrate or aluminum zirconium tetrachlorohydrex-glycine. The gel can also contain additional cosmetic ingredients such as emollients, colorants, fragrances, and preservatives.

It has been unexpectedly discovered that ester functionalized silicones of the present disclosure raises and improves the refractive index (RI) of the silicone significantly, which provides great benefit in personal care applications. That is, such formulations will show benefit as antiwhitening agents in antiperspirants and sunscreens.

These unique ester functionalized silicones maintain the same great surface tension property of silicone, i.e., provide the same spreading and silky feel as silicone in personal care formulations.

In addition to the two properties mentioned above, the silicone esters of the present disclosure provide enhanced formulation flexibility and provide ease to integrate various components that are not mixable otherwise.

Some examples of conventional gel antiperspirants and deodorants are set forth below:

Antiperspirant Water Phase Water 37.01% Aluminum Chlorohydrate 30.00% Ethanol 10.00% Propylene Glycol 4.99% Oil Phase Dimethicone 9.85% Cyclomethicone & Dimethicone Copolyol 8.00% Fragrance 0.15% Deodorant Water Phase Water 33.25% Sorbitol 14.00% Ethanol 12.00% Propylene Glycol 22.50% Triclosan 0.25% Sodium Hydroxide 0.02% Oil Phase Dimethicone 9.70% Cyclomethicone & Dimethicone Copolyol 8.00% Fragrance 0.30%.

International Patent Application No. WO 97/06777, which is incorporated herein by reference, also discloses a clear cosmetic gel composition which includes: (1) an aqueous phase containing water and at least one cosmetically active ingredient, (2) an oil phase containing a high refractive index material, (3) at least one coupling agent to bring the aqueous phase and the oil phase into a homogeneous composition, and (4) an alkoxylated, alkyl substituted siloxane surface active agent in an amount sufficient to form the composition into a water-in-oil emulsion. The oil phase includes a volatile silicone fluid, a non-volatile silicone fluid and an emollient. The emollient is preferably phenyl trimethicone.

U.S. Pat. No. 4,900,542 (Parrotta, Jr., et al.), which issued on Feb. 13, 1990 and which is incorporated herein by reference, discloses a process for preparing uniform, clear, microcrystalline emulsion antiperspirant compositions of gel-like consistency comprising: mixing the antiperspirant active material with water, charging the aqueous phase into an oil-alcohol phase containing a volatile silicone, a silicone emulsifier, a non-volatile emollient and a coupling agent, heating the resultant mixture with agitation until a uniform mixture is obtained, homogenizing the mixture and passing the homogenized mixture to a holding tank or directly to a filter.

The clear gel antiperspirants and deodorants described above are based on water-in-oil emulsions which are stabilized with a silicone surfactant. The silicone surfactant is commercially available as a 10 wt. % solution in a volatile silicone solvent, such as cyclomethicone (also known as decamethycyclopentasiloxane and/or octamethylcyclotetrasiloxane).

Esters have been used for a number of years for a variety of personal care applications including solids dispersion. The esters are fully esterified, i.e., for esters of polyhydric alcohols, nearly all the hydroxyl groups have been reacted with acids so that the hydroxyl number is generally less than about 5.

Zinc oxides have been used in the cosmetics industry as a potent sunscreen in concentrations in the range between 2 to 10% usually in oil-in-water formulations. To be effective it must be well dispersed to coat the skin evenly to prevent harmful ultraviolet (UV) rays from reaching the skin surface. If not dispersed effectively agglomeration occurs resulting in uneven distribution over the skin surface resulting in UV penetration of gaps in the surface layering.

The present inventors have discovered that utilization of a silicone based fluid made with partially esterified esters as a dispersing agent provides desired branching and reactive intermediates to effectively disperse inorganic solids, such as zinc oxide, thereby reducing the amount of zinc oxide required for use in personal care applications, such as sunscreens and color cosmetics.

SUMMARY OF THE INVENTION

A cosmetic composition comprising: (a) an aqueous phase comprising: (i) water, and (ii) at least one cosmetically active ingredient; (b) a coupling agent; and (c) an oil phase comprising: (i) an isoparaffin solvent, and (ii) a silicone-containing solvent having the formula:

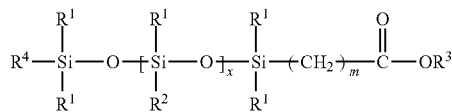

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

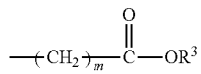

and a reverse ester thereof represented by the formula:

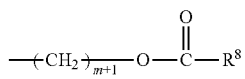

and the formula:

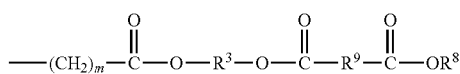

and a reverse ester thereof represented by the formula:

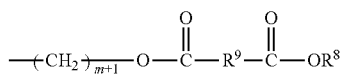

provided that if $R^1$ is anything but methyl or ethyl, then $R^2$ must be a methyl, ethyl or butyl, $R^3$ is derived from a partially esterified ester residue;

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, the ester-containing group and the compound derived from reverse esters thereof, m is an integer between about 5 to about 22; and x is an integer between about 0 to about 1000;

wherein the composition has at least 1 compound derived from the partially esterified ester-containing group or the reverse ester thereof.

Preferably, the isoparaffin solvent has a boiling range between about 100 to 340° C., wherein the isoparaffin constitutes between about 1 to 75% by weight, of the total of the oil phase.

The composition further comprising (d) a silicone-containing surfactant. The silicone-containing surfactant is an alkoxylated, alkyl substituted siloxane surface active agent. The silicone-containing surfactant is dimethicone copolyol or a mixture of dimethicone copolyol and cyclomethicone. The silicone-containing surfactant is present in an amount between about 0.2 to 2% by weight, of the total weight of the composition.

The coupling agent is present in an amount between about 10 to 30% by weight, of the total weight of the composition.

The isoparaffin solvent is a saturated aliphatic hydrocarbon containing at least one side chain, and wherein the total carbon atoms are in the range between about 8 to 20. The isoparaffin constitutes between about 25 to 50% by weight, of the total of the oil phase.

The composition further comprises at least one additional additive selected from the group consisting of: emollients, humectants, antiseptics, antioxidants, chelating agents, ultraviolet absorbers, colorants, fragrances and preservatives.

The composition is a deodorant, antiperspirant, sunscreen, insect repellent or anti-fungal agent.

A process for preparing a clear cosmetic composition comprising mixing the following: an aqueous phase comprising: (i) water, and (ii) at least one cosmetically active ingredient; a coupling agent; an oil phase comprising: (i) an isoparaffin solvent, and (ii) a silicone-containing solvent having the formula:

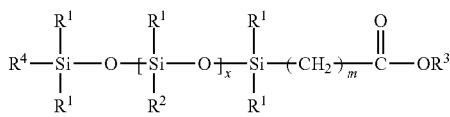

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

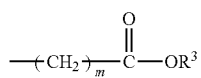

and a reverse ester thereof represented by the formula:

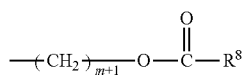

and the formula:

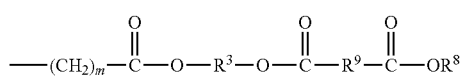

and a reverse ester thereof represented by the formula:

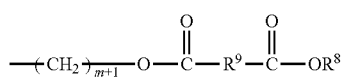

provided that if $R^1$ is anything but methyl or ethyl, then $R^2$ must be a methyl, ethyl or butyl, $R^3$ is derived from a partially esterified ester residue;

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, the ester-containing group and the compound derived from reverse esters thereof, m is an integer between about 5 to about 22; and x is an integer between about 0 to about 1000;

wherein the composition has at least 1 compound derived from the partially esterified ester-containing group or the reverse ester thereof.

Additionally, the cosmetic composition may also comprise: (a) an aqueous phase comprising: (i) water, and (ii) at least one cosmetically active ingredient; (b) a coupling agent; and (c) an oil phase comprising: (i) an isoparaffin solvent, and (ii) a silicone-containing solvent having the formula:

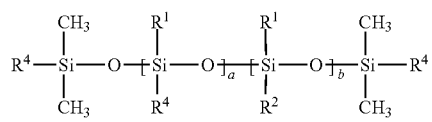

wherein $R^4$ is selected from the group consisting of: alkyl and a group represented by the formula:

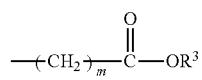

wherein:

a is an integer in the range between about 1 to about 20;

b is an integer in the range between about 0 to about 1000;

$R^3$ is a compound derived from a partially esterified ester residue; and m is an integer in the range between about 5 to about 22;

with the proviso that the $R^4$ groups are not all alkyls.

A composition for topical application to human skin, comprising a biologically active material and a cosmetically suitable carrier, wherein the cosmetically suitable carrier comprises: (a) an aqueous phase comprising: (i) water, and (ii) at least one cosmetically active ingredient; (b) a coupling agent; and (c) an oil phase comprising: (i) an isoparaffin solvent, and (ii) a silicone-containing solvent having the formula:

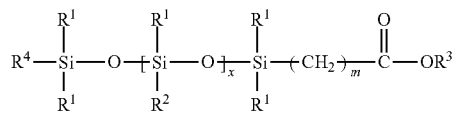

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

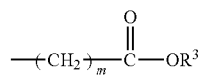

and a reverse ester thereof represented by the formula:

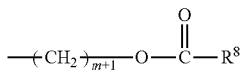

and the formula:

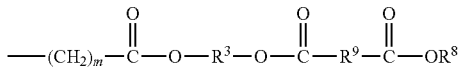

and a reverse ester thereof represented by the formula:

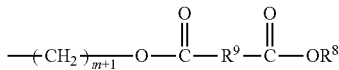

provided that if $R^1$ is anything but methyl or ethyl, then $R^2$ must be a methyl, ethyl or butyl, $R^3$ is derived from a partially esterified ester residue;

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, the ester-containing group and the compound derived from reverse esters thereof, m is an integer between about 5 to about 22; and x is an integer between about 0 to about 1000;

wherein the composition has at least 1 compound derived from the partially esterified ester-containing group or the reverse ester thereof.

Wherein the cosmetically suitable carrier exhibits at least one property selected from the group consisting of:
  substantially odor-free;
  a refractive index in the range between about 1.41_to about 1.46;
  solubility parameters in the range between about __7_to about__9+/−1.5_'d(i)@25° C. (cal/cc)^½_;
  viscosity in the range between about 35_to about __2450_cSt@25° C_;
  surface tension in the range between about 20 to about 23_dynes/cm_; and
  mixtures thereof.

The composition is one selected from the group consisting of: sunscreens, shampoos, lip balms, moisturizing lotions, and antiperspirants.

A method of making a composition for topical application to human skin, comprising a biologically active material and a cosmetically suitable carrier, comprising combining a mixed feed silicone ester into a carrier to produce a cosmetically suitable carrier, wherein the cosmetically suitable carrier comprises 5-05 wt % of the mixed feed silicone ester based on the total weight of the composition, wherein the mixed feed silicone ester comprises: a silicone-containing solvent having the formula:

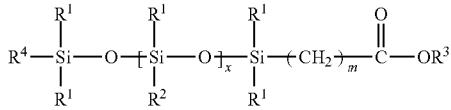

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

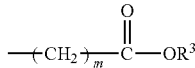

and a reverse ester thereof represented by the formula:

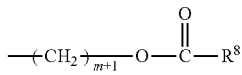

and the formula:

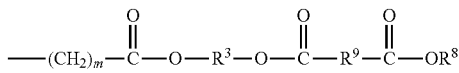

and a reverse ester thereof represented by the formula:

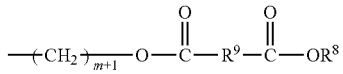

provided that if $R^1$ is anything but methyl or ethyl, then $R^2$ must be a methyl, ethyl or butyl, $R^3$ is derived from a partially esterified ester residue;

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, the ester-containing group and the compound derived from reverse esters thereof, m is an integer between about 5 to about 22; and x is an integer between about 0 to about 1000;

wherein the composition has at least 1 compound derived from the partially esterified ester-containing group or the reverse ester thereof.

BRIEF DESCRIPTION OF THE DRAWINGS

FIG. 2 is a table which provides comparative data relating to Brookfield viscosity when Z-Cote HP-1 (a zinc oxide product coated with triethyoxy caprylyl silane) is dispersed in conventional full ester products, such as PureSyn6, PureSyn 3E20 and MCP 2262, versus dispersion characteristics when dispersed in fluids formed from silicon-based partial esters according to the present disclosure.

FIG. 3 is a graph Brookfield viscosity versus solids loading amounts for the conventional full ester dispersions and fluid formed from silicon-based partial esters according to the present disclosure.

DETAILED DESCRIPTION OF THE PREFERRED EMBODIMENTS

Figure 1:
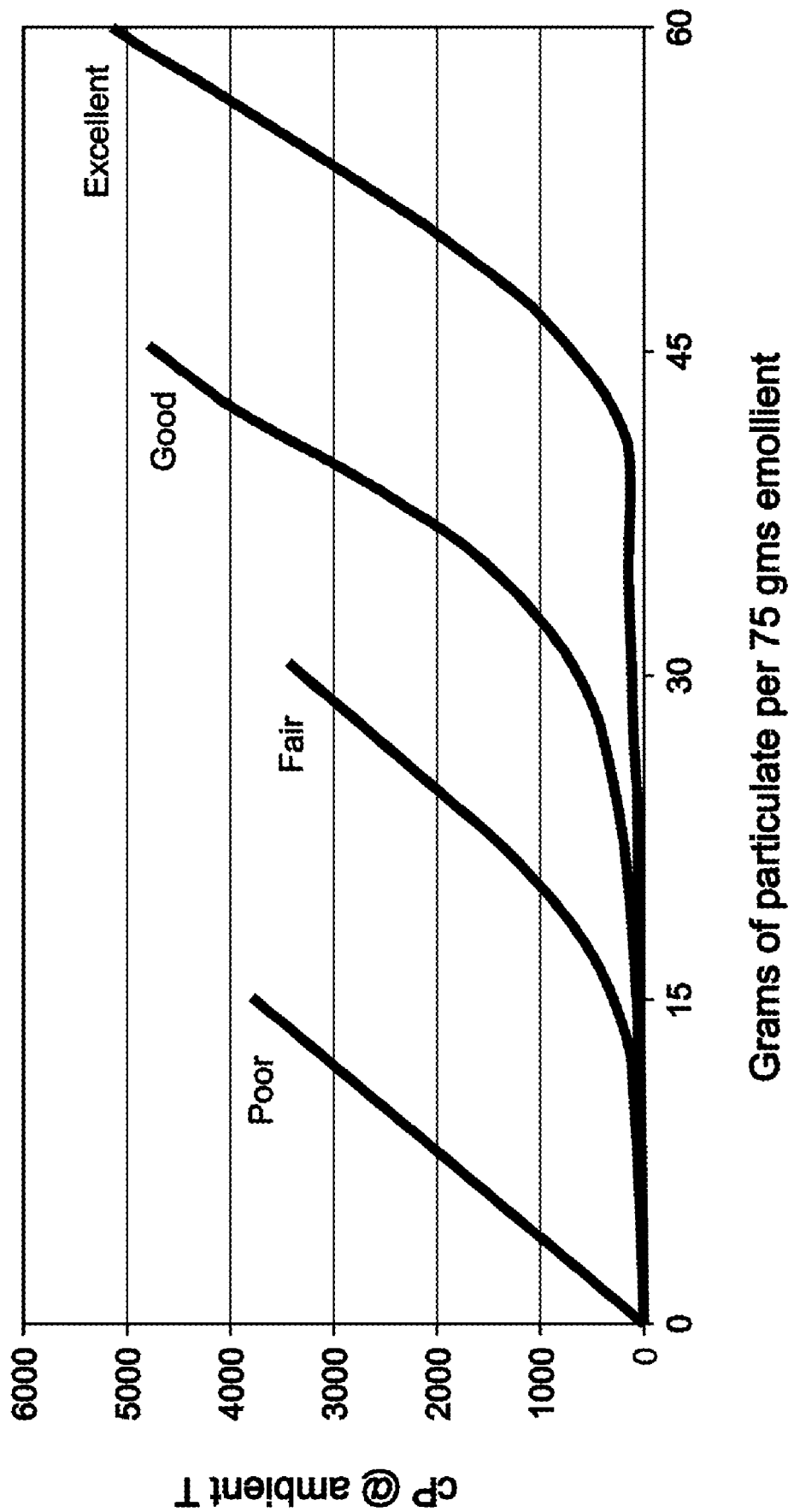
FIG. 1 is a graph depicting an arbitrary rating system that has been established to compare the efficacy of certain conventional dispersion compositions versus the compositions of the present disclosure.

A clear cosmetic composition comprising: (a) an aqueous phase comprising: (i) water, and (ii) at least one cosmetically active ingredient; (b) a coupling agent; (c) an oil phase comprising: (i) a silicone-containing solvent, and (ii) an isoparaffin solvent having a boiling range between about 100 to 340° C., wherein the isoparaffin constitutes between about 1 to 75% by weight, of the total of the oil phase; and (d) silicone-containing surfactant.

The silicone-containing surfactant is preferably an alkoxylated, alkyl substituted siloxane surface active agent, e.g., dimethicone copolyol or a mixture of dimethicone copolyol and cyclomethicone. This silicone-containing surfactant is present in an amount between about 0.2 to 2% by weight, of the total weight of the composition. The coupling agent is present in an amount between about 10 to 30% by weight, of the total weight of the composition.

The aqueous phase comprises water in an amount between about 20 to 70% by weight, of the total weight of the composition. The oil phase comprises a silicone-containing solvent which includes a volatile silicone fluid and a non-volatile silicone fluid. The volatile silicone fluid is preferably a cyclomethicone and the non-volatile silicone fluid is preferably dimethicone. The preferred mixture of the oil phase and the silicone-containing surfactant comprises between about 10 to 30% by weight, of the total weight of the composition, and the mixture of the aqueous phase and the coupling agent comprises between about 70 to 90% by weight, of the total weight of the composition.

Optionally, the isoparaffin can replace at least a portion of the dimethicone such that the oil phase has essentially the same viscosity as the original oil phase. The molecular weight of the dimethicone may need to be simultaneously increased to achieve this viscosity.

By isoparaffin is meant a saturated aliphatic hydrocarbon whose molecules have at least one carbon atom bonded to at least three other carbon atoms or at least one side chain (i.e., a molecule having one or more tertiary or quaternary carbon atoms), and preferably wherein the total number of carbon atoms per molecule is in the range between about 8 to 20, more preferably 10 to 20. Various isomers of each carbon number will typically be present in the solvent. The isoparaffins may also include cycloparaffins with branched side chains, generally as a minor component of the isoparaffin solvent. The isoparaffin solvent may contain molecules have a carbon number (e.g., a narrow cut such as isomers having a range between about $C_{10}$ to $C_{12}$, or a wide cut such as isomers having between about $C_{11}$ to $C_{18}$). The vapor pressure of the isoparaffin is also preferably not greater than 2 mm Hg at 20° C. for antiperspirant and deodorant products. Preferably, the isoparaffin constitutes between about 25 to 50% by weight, of the total of the oil phase.

The clear cosmetic composition of the present disclosure may further comprise at least one additional additive selected from the group consisting of: emollients, humectants, antiseptics, antioxidants, chelating agents, ultraviolet absorbers, colorants, fragrances and preservatives. This composition is preferably either a deodorant, antiperspirant, sunscreen, insect repellent or anti-fungal agent.

The present disclosure also pertains to a process for preparing a clear cosmetic composition comprising mixing the following: an aqueous phase comprising: (i) water, and (ii) at least one cosmetically active ingredient; a coupling agent; an oil phase comprising: (i) a silicone-containing solvent, and (ii) an isoparaffin solvent having a boiling range between about 100 to 340° C., wherein the isoparaffin constitutes between about 1 to 75% by weight, of the total of the oil phase; and silicone-containing surfactant.

Another embodiment of the present disclosure includes a clear cosmetic composition comprising: (a) an aqueous phase comprising: (i) water, and (ii) at least one cosmetically active ingredient; (b) a coupling agent; (c) an oil phase comprising: a silicone-containing solvent comprising a volatile silicone fluid and a non-volatile silicone fluid, and wherein at least a portion of the non-volatile silicone fluid is replaced with an isoparaffin solvent having a boiling range between about 200 to 340° C., wherein the viscosity of the non-volatile silicone/isoparaffin solution is in the range between about 10 to 100 cps at a temperature between about 20 to 25° C.; and (d) silicone-containing surfactant. Preferably, the volatile silicone fluid is cyclomethicone and the non-volatile silicone fluid is dimethicone. Optionally, the isoparaffin has a flash point in the range between about 60 to 150° C. and the non-volatile silicone fluid has a viscosity of no greater than 10,000 cSt.

Throughout the present disclosure, the present disclosure is described primarily in connection with a clear soft gel antiperspirant composition. However, the present disclosure is not limited to soft gel compositions or to antiperspirant compositions. For example, compositions according to the present disclosure can be clear deodorant compositions. Moreover, depending on additional or other active ingredients included in the composition, the composition can also be an emollient composition, an analgesic (methyl salicylate) composition, a sunscreen composition, etc. Various active materials incorporated in cosmetic compositions are disclosed in U.S. Pat. No. 4,322,400 to Yuhas, the contents of which are incorporated herein by reference in their entirety.

Throughout the present specification, "active antiperspirant" and "active deodorant" materials are discussed. Both types of materials contribute to reduction of body malodor. By reduction of body malodor, we mean that, generally, there is less body malodor after application of a composition to the person's skin as compared to the person's body malodor without application of the composition. Such reduction can be due to a masking of the malodor, absorption and/or chemical reaction of the malodorous material, reduction of levels of the bacteria producing the malodorous material, e.g., from perspiration, reduction of perspiration, etc. The antiperspirant active materials, when utilized in an antiperspirant effective amount in the composition, act to reduce body malodor by reducing production of perspiration; however, these antiperspirant active materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor absorbents, as antimicrobial agents, as agents chemically reacted with malodorous materials, etc.

A desired feature of the present disclosure is that a clear, or transparent, cosmetic composition (e.g., clear or transparent deodorant or antiperspirant gel composition) can be provided. The term clear or transparent (that is clarity), according to the present disclosure, is intended to connote its usual dictionary definition; thus, a clear, e.g., cosmetic composition at the present disclosure allows ready viewing of objects behind it. By contrast, a translucent composition allows light to pass through, but causes the light to be so scattered that it will be impossible to see clearly objects behind the translucent composition.

The present disclosure contemplates a clear cosmetic composition which is a water-in-oil emulsion. The aqueous phase of this emulsion contains water and at least one cosmetically active ingredient, with the cosmetically active ingredient being in the composition in an amount so as to have a cosmetic effect. The oil phase of the emulsion includes a high refractive index material (a material having a refractive index in the range of 1.40-1.50) and desirably also includes silicone surfactants, and preferably contains both volatile and non-volatile silicone solvents. Optionally, the compositions according to the present disclosure also include at least one coupling agent to bring the aqueous phase and the oil phase into a homogeneous composition. Moreover, the clear cosmetic composition of the present disclosure, which is in the form of a macro-emulsion as contrasted to a micro-emulsion, does not need to contain wax or gelling agents such as soaps, cellulosic materials or algenites.

The gel emulsions according to the present disclosure are stable and optically clear, are cosmetically elegant, and are capable of being delivered from a suitable applicator package. They are easily applied to the skin and have a smooth, silky feel and a cool sensation, yet are fast-drying and non-tacky. These compositions of the present disclosure may be prepared by a batch process, or a continuous or semi-continuous process, and the processes yield compositions which are stable, highly efficacious and possess excellent aesthetic qualities.

Where the composition is an antiperspirant gel composition, any of the known antiperspirant active materials can be utilized in the composition at the present disclosure. Suitable materials which may be mentioned by way of example include aluminum chlorohydrate, aluminum chloride, aluminum sesquichlorohydrate, aluminum-zirconium hydroxychlorides, complexes or adducts of the above-mentioned active ingredients with glycol, such as propylene glycol, and combinations thereof. Known aluminum-zirconium salts in combination with neutral amino acids, such as glycine (e.g., aluminum-zirconium tetrachlorohydroxy) can also be used. Generally, any of the Category I active antiperspirant ingredients, listed in the Food and Drug Administration's Monograph on Antiperspirant Drug Products for overall-the-counter human use (Oct. 10, 1973) can be used. In addition, any new ingredient, not listed in the Monograph, such as aluminum nitrohydrate and its combination with zirconyl hydroxychlorides and nitrates, or aluminum-stannous chlorohydrates, can be incorporated as an antiperspirant active ingredient in antiperspirant compositions according to the present disclosure.

The preferred antiperspirant materials include aluminum zirconium tetrachlorohydrate and aluminum chlorohydrate.

The amount of active component that can be used will vary with the particular active ingredient incorporated. As a general rule, an antiperspirant product should contain an active antiperspirant material in an amount anywhere from about 10% to about 35% by weight, of the total weight of the composition, more preferably from about 20% to about 30% by weight, of the total weight of the composition. The active antiperspirant material utilized in the compositions of the present disclosure can be pre-dissolved in water or in another solvent (for example, in propylene glycol) or can be in powdered form, and may be buffered or unbuffered. Preferably, the antiperspirant materials are present in solution in a solvent therefor.

Where a deodorant active material is utilized, any deodorant active material which can be dissolved in the aqueous phase can be utilized. Illustratively, the deodorant active material can be 2,4,4'-trichloro-2'-hydroxy diphenyl ether (triclosan), and/or benzethonium chloride. Where the deodorant ingredient is used in place of the antiperspirant active ingredient, a deodorant gel composition (rather than an antiperspirant gel composition) would be provided.

Amounts of cosmetically active ingredients incorporated are those sufficient to have a cosmetic effect. For example, where a deodorant active ingredient such as triclosan is incorporated, amounts thereof as conventionally used in the art can be incorporated in the composition according to the present disclosure.

The aqueous phase includes one or a combination of various polar species, and includes at least water (refractive index of 1.3333). Other polar species include polyhydric alcohols and derivatives thereof (e.g., esters and ethers thereof). Illustratively, water can be included in the composition in an amount in the range of 20% to 70% by weight, of the total weight of the composition.

At least one coupling agent is included in the composition of the present disclosure. Such coupling agent is illustratively (but not limited to) the following:

Coupling Agents Ethyl alcohol Ethylene glycol monoethyl ether 2-ethylhexanol Diethylene glycol monoethyl ether Ethylene carbonate Propoxylated oleyl alcohol N-methylglucamine Butyl stearate Linear ethoxylated polymer of Butyl myristate methanol Isopropyl alcohol SD-40 alcohol PPG-(2-5) lanolate PPG (2-8) myristyl ether PPG-(2-8) isostearate PPG (2-8) lauryl ether Propylene glycol (2) methyl ether Dipropylene glycol PPG-(2-3) methyl ether PPG (2-10) cetyl ether PPG-14 butyl ether PEG-6 diisopropyl adipate Ethoxylated (2-20 moles) glucose Methoxy PEG-22 dodecyl-glycol Propoxylated (2-20 moles) glucose copolymer PPG-15 Stearyl ether PEG-30 Glyceryl monoacetate PPG-(5-20) methyl glucose ether Sorbitol Isoprene glycol PEG-3 oleyl ether phosphate Propylene carbonate PEG-(2-5) oleyl ether Glycerine This coupling agent acts to stabilize the emulsion and also acts as a clarifying agent. Moreover, various of these coupling agents, such as SD-40 alcohol, aid in drying and has a cooling effect, providing advantageous aesthetic properties for the composition.

The coupling agent is preferably a low molecular weight alcohol such as, but not limited to, an alcohol having from about 2 to about 10 carbon atoms, preferably from about 2 to about 4 carbon atoms; or a glycol such as, but not limited to, propylene glycol, ethylene glycol, isoprene glycol and dipropylene glycol; glycerine, sorbitol and/or propylene carbonate. The coupling agent can be one compound or a mixture of compounds.

Illustratively, the coupling agent is present in an amount of from about 10% to about 30% by weight, preferably from about 14% to about 25% by weight, of the total weight of the composition.

The oil phase according to the present disclosure is desirably, a silicone oil/isoparaffin solution, so as to provide a water-in-oil emulsion. The total of oil phase and siloxane surface active agent preferably makes up from about 8% to about 30% by weight, of the total weight of the composition. This surface active agent is an emulsifier which, when properly mixed with the aqueous phase components, oil phase components and coupling agents, yields a water-in-oil emulsion. The oil phase is desirably a blend of liquids.

The oil phase can include, illustratively, a silicone-containing solvent having the general formula:

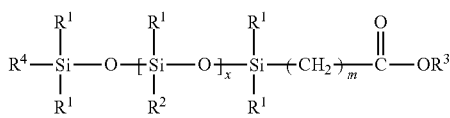

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, an ester-containing group represented by the formula:

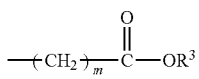

and a reverse ester thereof represented by the formula:

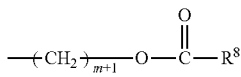

and the formula:

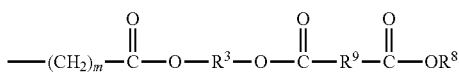

and a reverse ester thereof represented by the formula:

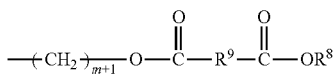

provided that if $R^1$ is anything but methyl or ethyl, then $R^2$ must be a methyl, ethyl or butyl, $R^3$ is derived from a partially esterified ester residue, e.g., for a partially esterified trimetholpropane shown here, the residue is the structure without the remaining free hydroxyl group

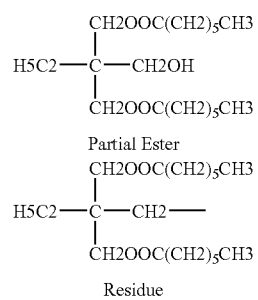

wherein this case the two esterified groups on the molecule have been reacted with heptanoic acid.

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, said ester-containing group and said compound derived from reverse esters thereof, m is an integer between about 5 to about 22; and x is an integer between about 0 to about 1000;

wherein said composition has at least 1 compound derived from said partially esterified ester-containing group or and said reverse ester thereof.

Preferably, $R^1$ and $R^2$ are both methyl groups and m is an integer between about 10 to about 14, preferably m is 10. Moreover, x is an integer in the range between about 6 to about 110, preferably between about 6 to about 50.

The compound derived from said partially esterified ester residue is a partially esterified alcohol. The mono-hydroxy-terminated partially esterified alcohol is derived from a polyfunctional alcohol represented by the formula:

wherein:

$R^5$ is an n-functional hydrocarbon; and n is from about 2 to about 8, preferably between about 2 to about 4.

The functional alcohol is preferably selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof. The preferred functional alcohol is trimethylolpropane.

The compound derived from said partially esterified ester residue is a partially esterified acid. The mono-hydroxy-terminated partially esterified acid is derived from multi-functional acids. The functional acid can be selected from the group consisting of any C2 to C12 diacids, e.g., adipic, azelaic, sebacic, and dodecanedioc, succinic acid, glutaric acid, maleic acid, phthalic acid, trimellitic acid, nadic acid, methyl nadic acid, hexahydrophthalic acid and mixtures thereof.

Anhydrides of polybasic acids can be used in place of the multifunctional acids. The functional anhydride is selected from the group consisting of: succinic anhydride, glutaric anhydride, adipic anhydride, maleic anhydride, phthalic anhydride, trimellitic anhydride, nadic anhydride, methyl nadic anhydride, hexahydrophthalic anhydride, and mixtures thereof.

$R^4$ is preferably a group represented by the formula:

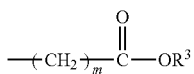

wherein:
$R^3$ is a compound derived from a partially esterified ester residue;
m is an integer in the range between about 5 to about 22; and
x is an integer in the range between about 0 to about 1000, or a reverse ester thereof represented by the formula:

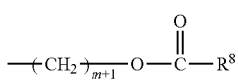

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue.

Alternatively, $R^4$ is a methyl group.

The silicone-containing solvent may also be represented by the formula:

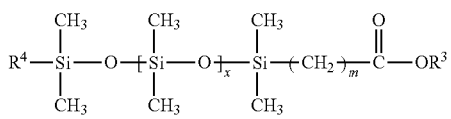

wherein:
$R^4$ is selected from the group consisting of methyl and a group represented by the formula:

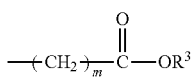

$R^3$ is a compound derived from a partial ester residue;
m is 10; and
x is an integer in the range between about 0 to about 1000, preferably about 6 to about 110.

$R^4$ is preferably a group represented by the formula:

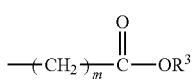

wherein $R^3$ is a compound derived from a partially esterified ester residue. The partially esterified ester residue is derived from a mono-hydroxy-terminated partially esterified alcohol. The mono-hydroxy-terminated partially esterified alcohol is derived from di-, tri- or tetra-functional alcohol represented by the formula:

$R^5(OH)_n$ wherein:
$R^5$ is an n-functional hydrocarbon residue; and
n is an integer in the range between about 2 to about 8, preferably between about 2 to about 4.

Preferably, the di-, tri- or tetra-functional alcohol is selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

Preferably, the functional alcohol is trimethylolpropane and $R^4$ is a group represented by the formula:

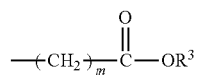

wherein:
$R^3$ is a compound derived from a partially esterified ester residue;
m is an integer in the range between about 5 to about 22; and
x is an integer in the range between about 0 to about 1000, or a reverse ester thereof represented by the formula:

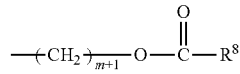

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue. Alternatively, $R^4$ is a methyl group.

The partially esterified ester is represented by the formula:

$(R^7COO)_{n-1}R^6(OH)$ wherein:
$R^6$ is an (n-1)-functional hydrocarbon residue group;
$R^7$ is a hydrocarbyl group; and
n is an integer in the range between about 2 to about 8.

According to another embodiment of the present disclosure, a silicone composition is represented by the formula:

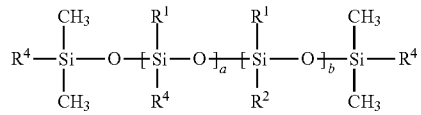

wherein $R^4$ is selected from the group consisting of: alkyl and a group represented by the formula:

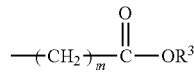

wherein:
a is an integer in the range between about 1 to about 20;
b is an integer in the range between about 0 to about 1000;
$R^3$ is a compound derived from a partially esterified ester residue; and
m is an integer in the range between about 5 to about 22; with the proviso that the $R^4$ groups are not all alkyls.

The alkoxylated, alkyl substituted siloxane surface active agent is preferably, but not limited to, a dimethicone copolyol. An illustrative alkoxylated silicone-containing surfactant utilizable according to the present disclosure is cetyl dimethicone copolyol referred to in U.S. Pat. No. 5,162,378 to Guthauser. Illustratively, the alkoxylated, alkyl substituted siloxane surface active agent is included in the composition in an amount of 0.2% to 2% by weight, of the total weight of the composition.

A specific cyclomethicone-dimethicone copolyol fluid which can be utilized to provide the alkoxylated silicone containing surface active agent is a mixture of cyclomethicone and dimethicone copolyol designated as DC3225C from Dow Corning Corp or SF1328 from General Electric Company. This is a polyether substituted silicone of cyclomethicone and dimethicone copolyol (refractive index (RI) =1.3994). This DC3225C, which is an emulsifying agent, is useful for preparing stable water-in-oil emulsions where a silicone makes up a large portion of the oil phase, and is a dispersion of a silicone surfactant (dimethicone copolyol) (10% by wt.) in cyclomethicone (Dow Corning 344 Fluid) (90% by wt.).

The mixture of cyclomethicone and dimethicone copolyol fluid is present in the composition, illustratively, in an amount of from about 4% to about 20% by weight, of the total weight of the composition. The unique aspect according to the present disclosure is that between 25-50% of the cyclomethicone in the dimethicone copolyol dispersion is replaced with at least one isoparaffin without any concomitant loss of properties, but with the added cost benefits associated with the use of much cheaper isoparaffins.

Various materials which can be incorporated in the water-based phase and in the oil-based phase are listed in International Patent Application Publication No. WO 97/06777, which is incorporated herein by reference, for example, emollients, humectants, antiseptics, preservatives, antioxidants, chelating agents, and U.V. absorbers.

While not limiting, in preferred embodiments the mixture of oil phase and alkoxylated, alkyl substituted siloxane surface active agent comprises from about 10% to about 30% by weight, of the total weight of the composition, and the combination of aqueous phase and coupling agents make up from about 70% to about 90% by weight, of the total weight of the composition.

The metal oxide inorganic compound is at select one selected from the group consisting of uncoated zinc oxide coated with triethoxy caprylyl silane and titanium dioxide.

In addition the emollient formed by admixing the metal oxide inorganic compound with the silicone compound formed partial esters exhibit the following properties: a Brookfield viscosity at ambient temperature in the range between about 100_to about 25000 cP at ambient temperature.

In a preferred embodiment, R1 and R2 are independently selected from hydrogen, alkyl of 1 to 45 carbon atoms, substituted alkyl of 1 to 45 carbon atoms optionally substituted by one or more fluorine atoms and aryl. More preferably, R1 and R2 are both methyl groups.

Preferably, m is from about 10 to about 14, most preferably m is 10.

Preferably, x is from about 6 to about 110, most preferably x is from about 6 to about 50.

R3 is preferably a mono-hydroxy-terminated partially esterified ester.

The mono-hydroxy-terminated partially esterified ester residue is derived from a mono-hydroxy-terminated partially esterified alcohol. That is, the mono-hydroxy-terminated partially esterified alcohol is derived from di-, tri- or tetra-functional alcohol represented by the formula:

wherein:
$R^5$ is an n-functional hydrocarbon residue; and
n is from about 2 to about 8, preferably from 2 to 4.

The functional alcohol is preferably selected from ethylene glycol, propylene glycol, butylene glycol, polyethylene glycol, neopentyl glycol polypropylene glycol, glycerin, trimethylolethane, trimethylolpropane, pentaerythritol, di-pentaerythritol, tri-pentaerythritol, and a mixture there, most preferably the functional alcohol is trimethylolpropane.

$R^4$ is a group represented by the formula:

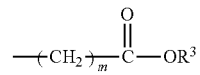

wherein:
$R^3$ is a compound derived from a partially esterified ester residue;
m is an integer in the range between about 5 to about 22; and
x is an integer in the range between about 0 to about 1000, or a reverse ester thereof represented by the formula:

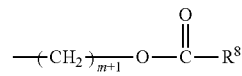

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue. Alternatively, $R^4$ is a methyl group.

The silicone composition represented by the formula:

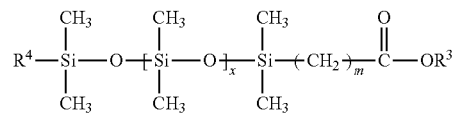

wherein:
$R^4$ is selected from the group consisting of methyl and a group represented by the formula:

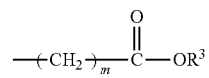

$R^3$ is a monohydroxy-terminated partial ester residue;
m is 10; and
x is from about 6 to about 110, preferably from 6 to about 50.

$R^4$ can be a group represented by the formula:

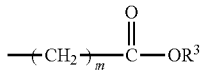

wherein $R^3$ is derived from a partially esterified ester residue, e.g., for a partially esterified trimetholpropane shown here, the residue is the structure without the remaining free hydroxyl group

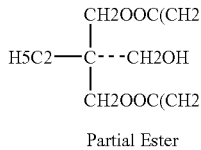 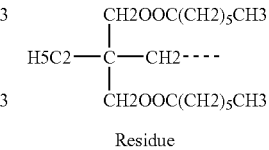

Partial Ester      Residue

Where in this case the two esterified groups on the molecule have been reacted with heptanoic acid.

The mono-hydroxy-terminated partially esterified ester residue is derived from a mono-hydroxy-terminated partially esterified alcohol.

Preferably, the mono-hydroxy-terminated partially esterified alcohol is derived from di-, tri- or tetra-functional alcohol represented by the formula:

$R^5(OH)_n$ wherein:

$R^5$ is an n-functional hydrocarbon residue; and n is from about 2 to about 8, preferably from 2 to 4.

Preferably, the di-, tri- or tetra-functional alcohol is selected from ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof, most preferably trimethylolpropane.

Alternatively, the mono-hydroxy-terminated partially esterified ester is represented by the formula:

$(R^7COO)_{n-1}R^6(OH)$ wherein:

$R^6$ is an (n-1)-functional hydrocarbon residue group;

$R^7$ is a hydrocarbyl group; and n is from about 2 to about 4.

Preferably, the vinyl-terminated carboxylic acid ester of a partially esterified ester is represented by the formula:

$CH_2{=}CH{-}(CH_2)_{m\text{-}2}{-}COOR^6(OOCR^7)_{n-1}$ wherein:

$R^6$ is an (n-1)-functional hydrocarbon residue;

$R^7$ is a hydrocarbyl group;

m is about 5 to about 22; and n is from about 2 to about 8, preferably from about 2 to about 4.

Preferably, the vinyl-terminated carboxylic acid ester of a partially esterified ester is formed by reacting a mono-hydroxy-terminated partially esterified ester with either an olefinic acid, methyl ester or anhydride.

Preferably, the vinyl-terminated carboxylic acid ester of a partially esterified ester is hydrosilated with a hydride terminated polysiloxane represented by the formula:

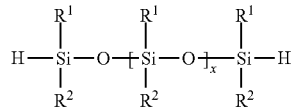

wherein:

$R^1$ and $R^2$ are independently selected from methyl, ethyl and phenyl; and x is from about 0 to about 1000.

Alternatively, the hydride can be located internally.

Preferably, the vinyl-terminated carboxylic acid ester of a partially esterified ester is represented by the following formula:

$CH_2{=}CH{-}(CH_2)_{m\text{-}2}{-}COOR^3$ $R^3$ is derived from a partially esterified ester residue, e.g., for a partially esterified trimetholpropane shown here, the residue is the structure without the remaining free hydroxyl group.

Partial Ester      Residue where in this case the two esterified groups on the molecule have been reacted with heptanoic acid; and m is from about 5 to about 22.

The silicone ester compound formed according to the preferred method has the formula:

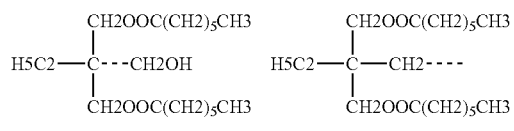

wherein:

$R^1$ and $R^2$ are independently selected from methyl, ethyl and phenyl;

$R^3$ is derived from a partially esterified ester residue, e.g., for a partially esterified trimetholpropane shown here, the residue is the structure without the remaining free hydroxyl group

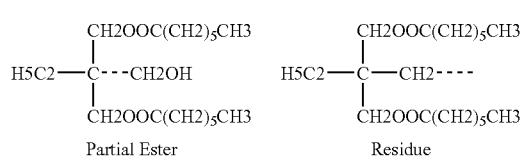

Partial Ester      Residue where in this case the two esterified groups on the molecule have been reacted with heptanoic acid;

m is from about 5 to about 22; and x is from about 0 to about 1000.

Preferably, the silicone hydride precursor is represented by the formula:

$$H-\underset{R^2}{\overset{R^1}{\underset{|}{Si}}}-O-(\underset{R^2}{\overset{R^1}{\underset{|}{Si}}}-O)_x-\underset{R^2}{\overset{R^1}{\underset{|}{Si}}}-H$$

wherein:
$R^1$ and $R^2$ are independently selected from methyl, ethyl and phenyl; and
x is from about 0 to about 1000.
Alternatively, the hydride can be located internally.

In a preferred embodiment, the silicone hydride precursor has one or more block polymers or block copolymers in the backbone. For example, the backbone group represented by the formula:

$$-(\underset{R^2}{\overset{R^1}{\underset{|}{Si}}}-O)_x-$$

can have one or more of the same or different block copolymers and the silicone ester compound can be represented by the formula:

$$R^4-\underset{CH_3}{\overset{CH_3}{\underset{|}{Si}}}-O-(\underset{R^4}{\overset{R^1}{\underset{|}{Si}}}-O)_a-(\underset{R^2}{\overset{R^1}{\underset{|}{Si}}}-O)_b-\underset{CH_3}{\overset{CH_3}{\underset{|}{Si}}}-R^4$$

wherein $R^4$ is selected from alkyl and a group represented by the formula:

$$-(CH_2)_m-\overset{O}{\underset{||}{C}}-OR^3$$

a is an integer from 1 to 20;
b is an integer from 0 to 200;
$R^3$ is derived from a partially esterified ester residue, e.g., for a partially esterified trimetholpropane shown here, the residue is the structure without the remaining free hydroxyl group

```
        CH2OOC(CH2)5CH3                CH2OOC(CH2)5CH3
        |                              |
H5C2----C---CH2OH              H5C2----C----CH2----
        |                              |
        CH2OOC(CH2)5CH3                CH2OOC(CH2)5CH3

Partial Ester                  Residue
``` where in this case the two esterified groups on the molecule have been reacted with heptanoic acid; and
m is an integer from about 5 to about 22;
with the proviso that all $R^4$ groups are not alkyl.

The hydride terminated polysiloxane and vinyl terminated carboxylic ester of a partially esterified ester are heated to 80-120° C. and a platinum hydrosilation catalyst such as hloroplatinic acid or any other platinum catalyst familiar to those skilled in the art is added up to about 100 ppm. Optionally a solvent such as toluene, xylene, IPA or any other solvent that is familiar to those skilled in the art can be used. The reaction is heated at 80-120° C. until all silicone hydride is consumed, which usually takes about 2-8 hours. If a solvent is used, it is then stripped under vacuum.

Esters have been used for a number of years for a variety of applications including lubricants. In most cases, the esters are fully esterified. For esters of polyhydric alcohols, nearly all the hydroxyl groups have been reacted with acids so that the hydroxyl number is generally less than about 5 (<~5).

By limiting the extent of the reaction, for example, by shortening the reaction time or starving the reaction mixture of at least one of the reactants, partial esters can be created. Polyol ester compositions having unconverted hydroxyl groups have been used as lubricant base stocks. Their preparation and uses have been described in U.S. Pat. No. 5,698,502.

Partially reacted esters provide the desired reactive intermediate functional groups for hydrosilation and branching. For example, certain polyhydric alcohols, such as, pentaerythritol, provide a neopentyl carbon with a $CH_2OH$ group attached. Reacting an acid to one, two, or three of these functional groups provides the partial ester.

Partially esterified esters having only one free hydroxyl group are preferred, preferably about 0.7 hydroxyl groups. This reduces opportunities for cross-linking during the hydrosilation process. An example of a preferred hydrosilation process is set forth in U.S. Pat. No. 5,561,231, which is incorporated herein by reference in its entirety.

Other multifunctional alcohols include trimethylolpropane, pentaerythritols, neopentyl glycol, sorbitol and mixtures thereof.

In the practice of the invention, the alcohols are allowed to react with carboxylic acids to produce partially or fully esterified esters or mixtures of partially and fully esterified esters. The acid can be a monocarboxylic acid, such as, octanoic acid, and can vary in chain length to provide the desired branching in the final product. The acid can also be a multifunctional acid. Examples of such multi-functional acids include adipic acid.

Silicone ester compounds with a range of molecular weights can be prepared by reacting the ester created from esterification of a vinyl containing molecule with an esterified ester with a silicone backbone. The resulting compounds have unique properties that make them useful in a number of applications.

The present disclosure further contemplates the use of more complex esters, such as, complex esters resulting from the reaction of polyhydric alcohol with a multifunctional acid followed by further reaction with a monofunctional alcohol to produce a partially esterified ester.

The partially esterified esters can be reacted with an olefinic acid, such as, undecylenic acid and thereafter hydrosilated, for example, with a hydride terminated polysiloxane.

The number of Si atoms in the above molecule represents a preferred range. However, the number of Si atoms could be higher, by way of examples only, as high as a 1000.

Monohydroxy-terminated partial ester can be represented by the formula:

$$R^3-OH$$

wherein $R^3$ is derived from a partially esterified ester residue, e.g., for a partially esterified trimetholpropane shown here, the residue is the structure without the remaining free hydroxyl group

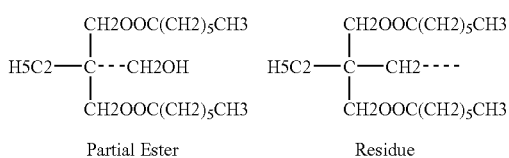

Partial Ester | Residue where in this case the two esterified groups on the molecule have been reacted with heptanoic acid.

Thus, the present disclosure provides a silicone ester compound with esterified groups represented by the formula:

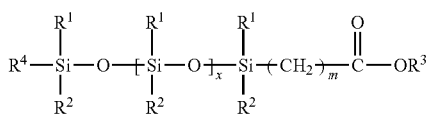

wherein:

$R^1$ and $R^2$ are independently selected from methyl, ethyl and phenyl;

$R^4$ is selected from methyl, ethyl, phenyl and a group represented by the formula:

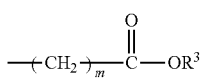

$R^3$ is derived from a partially esterified ester residue, e.g., for a partially esterified trimetholpropane shown here, the residue is the structure without the remaining free hydroxyl group.

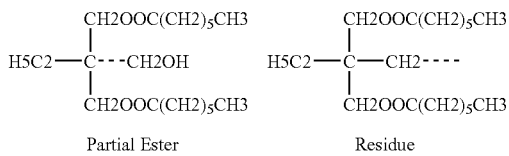

Partial Ester | Residue where in this case the two esterified groups on the molecule have been reacted with heptanoic acid;

m is an integer from 5 to 22; and x is an integer from about 0 to about 1000.

In a preferred embodiment of the above silicone fluids, $R^1$ and $R^2$ are both methyl groups, m is from 10 to 14 and, more preferably, m is 10, x is from about 6 to about 110 and, more preferably, x is from about 6 to about 50.

Typically, $R^3$ is a mono-hydroxy-terminated partially esterified ester residue which is derived from a mono-hydroxy-terminated partially esterified alcohol.

The mono-hydroxy-terminated partially esterified alcohol is preferably derived from di-, tri- or tetra-functional alcohol represented by the formula:

$R^5(OH)_n$ wherein:

$R^5$ is an n-functional hydrocarbon residue; and n is from 2 to 8, preferably from 2 to 4.

Preferably, the di-, tri- or tetra-functional alcohol is ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, or a mixture thereof Preferably, the di, tri- or tetra-functional alcohol is trimethylolpropane.

The R4 group can be either a methyl group or it can be a group represented by the formula:

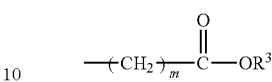

wherein $R^3$ is derived from a partially esterified ester residue, e.g., for a partially esterified trimetholpropane shown here, the residue is the structure without the remaining free hydroxyl group

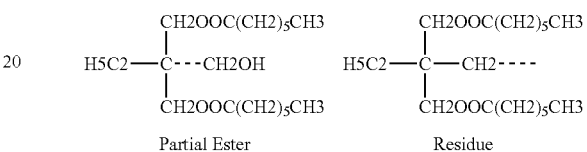

Partial Ester | Residue where in this case the two esterified groups on the molecule have been reacted with heptanoic acid;

m is an integer from 5 to 22; and x is an integer from about 0 to about 1000.

In a more preferred embodiment, the silicone ester compound is represented by the formula:

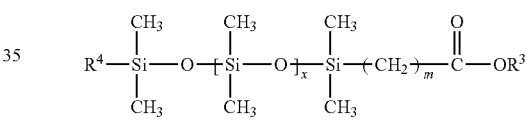

wherein:

$R^4$ is a methyl or a group represented by the formula:

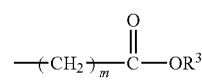

$R^3$ is derived from a partially esterified ester residue, e.g., for a partially esterified trimetholpropane shown here, the residue is the structure without the remaining free hydroxyl group

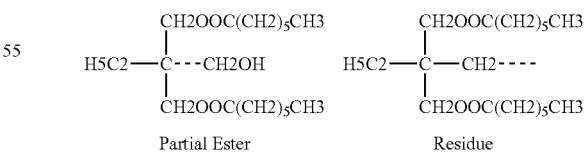

Partial Ester | Residue where in this case the two esterified groups on the molecule have been reacted with heptanoic acid;

m is 10; and x is from about 6 to about 110.

More preferably, x is from about 6 to about 50, $R^3$ is a mono-hydroxy-terminated partially esterified ester residue derived from a mono-hydroxy-terminated partially esterified alcohol which, in turn, is derived from di-, tri- or tetra-functional alcohol represented by the formula:

$$R^5(OH)_n$$

wherein:
$R^5$ is an n-functional hydrocarbon residue; and
n is an integer from 2 to 8, preferably from 2 to 4.

Examples of the di-, tri- or tetra-functional alcohols include ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

Trimethylolpropane is preferred.

The mono-hydroxy-terminated partially esterified ester can be represented by the formula:

$$(R^7COO)_{n-1}R^6(OH)$$

wherein:
$R^6$ is an (n-1)-functional hydrocarb residue group;
$R^7$ is a hydrocarbyl group; and
n is an integer from 2 to 8, preferably from 2 to 4.

The present disclosure further provides a process for preparing a silicone ester compound including the step of contacting:

(i) a hydride terminated polysiloxane represented by the formula:

$$H-\underset{R^2}{\overset{R^1}{\underset{|}{\overset{|}{Si}}}}-O-\left[\underset{R^2}{\overset{R^1}{\underset{|}{\overset{|}{Si}}}}-O\right]_x-\underset{R^2}{\overset{R^1}{\underset{|}{\overset{|}{Si}}}}-H$$

and (ii) a vinyl-terminated carboxylic acid ester of partially esterified ester represented by the formula:

$$CH_2=CH-(CH_2)_{m-2}-COOR^3$$

at a temperature and for a period of time sufficient to produce a silicone ester compound represented by the formula:

$$R^3O-\overset{O}{\underset{}{\overset{\|}{C}}}-(CH_2)_m-\underset{R^2}{\overset{R^1}{\underset{|}{\overset{|}{Si}}}}-O-\left[\underset{R^2}{\overset{R^1}{\underset{|}{\overset{|}{Si}}}}-O\right]_x-\underset{R^2}{\overset{R^1}{\underset{|}{\overset{|}{Si}}}}-(CH_2)_m-\overset{O}{\underset{}{\overset{\|}{C}}}-OR^3$$

wherein:
$R^1$ and $R^2$ are independently selected from methyl, ethyl and phenyl;
$R^3$ is derived from a partially esterified ester residue, e.g., for a partially esterified trimetholpropane shown here, the residue is the structure without the remaining free hydroxyl group $$\underset{\text{Partial Ester}}{H5C2-\underset{CH2OOC(CH2)_5CH3}{\overset{CH2OOC(CH2)_5CH3}{\underset{|}{\overset{|}{C}}}}-CH2OH} \quad \underset{\text{Residue}}{H5C2-\underset{CH2OOC(CH2)_5CH3}{\overset{CH2OOC(CH2)_5CH3}{\underset{|}{\overset{|}{C}}}}-CH2----}$$

where in this case the two esterified groups on the molecule have been reacted with heptanoic acid;
m is an integer from 5 to 22; and
x is an integer from about 0 to about 1000.

In a preferred embodiment of the process described above, $R^1$ and $R^2$ are both methyl groups, m is from 10 to 14, more preferably m is 10, x is from about 6 to about 110, and more preferably, x is from about 6 to about 50.

Preferably, R3 is derived from a partially esterified ester residue, e.g., for a partially esterified trimetholpropane shown here, the residue is the structure without the remaining free hydroxyl group.

$$\underset{\text{Partial Ester}}{H5C2-\underset{CH2OOC(CH2)_5CH3}{\overset{CH2OOC(CH2)_5CH3}{\underset{|}{\overset{|}{C}}}}-CH2OH} \quad \underset{\text{Residue}}{H5C2-\underset{CH2OOC(CH2)_5CH3}{\overset{CH2OOC(CH2)_5CH3}{\underset{|}{\overset{|}{C}}}}-CH2----}$$

where in this case the two esterified groups on the molecule have been reacted with an acid, derived from a mono-hydroxy-terminated partially esterified alcohol derived from di-, tri- or tetra-functional alcohol represented by the formula:

$$R^5(OH)_n$$

wherein:
$R^5$ is an n-functional hydrocarbon residue; and
n is an integer from 2 to 8, preferably from 2 to 4.

The di-, tri- or tetra-functional alcohol can be ethylene glycol, propylene glycol, butylene glycol, polyethylene glycol, neopentyl glycol polypropylene glycol, glycerin, trimethylolethane, trimethylolpropane, pentaerythritol, di-pentaerythritol, tri-pentaerythritol, or a mixture thereof.

Trimethylolpropane is preferred.

The mono-hydroxy-terminated partially esterified ester is represented by the formula:

$$(R^7COO)_{n-1}R^6(OH)$$

wherein:
$R^6$ is an (n-1)-functional hydrocarbon residue group;
$R^7$ is a hydrocarbyl group; and
n is from 2 to 8, preferably from 2 to 4.

The vinyl-terminated carboxylic acid ester of partially esterified ester can be represented by the formula:

$$CH_2=CH-(CH_2)_{m-2}-COOR^6(OOCR^7)_{n-1}$$

wherein:
$R^6$ is an (n-1)-functional hydrocarbon residue group;
$R^7$ is a hydrocarbyl group;
m is an integer 5 to 22; and
n is an integer from 2 to 8, preferably from 2 to 4.

It is possible to have a much more complex structure at one or more positions of the silicone fluid. For example, the ester intermediate can have more than one free hydroxyl groups present. In this case, cross-linking via the ester groups is possible. Thus, each free hydroxyl group could react with the olefinic acid and the resulting product could then react with two silicone compounds.

The process for preparing a silicone fluid includes the step of contacting the hydride terminated polysiloxane and the vinyl-terminated carboxylic acid ester of partially esterified ester described herein. The hydride terminated polysiloxane and vinyl terminated carboxylic ester of a partially esterified ester are heated to 80-120° C. and a platinum hydrosilation catalyst such as chloroplatinic acid or any other platinum catalyst familiar to those skilled in the art is added at 5 to 100 ppm. Optionally, a solvent such as toluene, xylene, IPA or any other solvent that is familiar to those skilled in the art can be used. The reaction is heated at 80-120° C. until all silicone hydride is consumed, which usually takes about 2-8 hours. If a solvent is used, it is then stripped under vacuum.

A functionalized ester was prepared by hydrosilating
(1) an ester of undecylenic acid reacted with a partial ester of trimethylolpropane with a linear octanoic/decanoic acid blend with a
(2) with a hydride terminated polysiloxane represented by the following formula

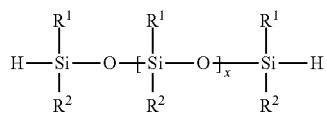

wherein:
$R^1$ and $R^2$ are methyl groups and x is approximately 45. The fluid viscosities and viscosity index (VI) of the product and of the functionalized esters are compared to the values that would be observed for the free ester and the hydride terminated polysiloxane in the following table:

| | Material | | | |
|---|---|---|---|---|
| | C8/10 based Trimethylol-propane | functionalized Di-45 w/Ester | Calculated functionalized Di-45 ester | Silicone Di-45 ester{3} |
| Free Ester content, % | 100 | 18.8 | 0 | 0 |
| Kinematic Vis, cSt {1} & {2} | | | | |
| 40° C. | 19 | 186 | 315.6 | 38.3 |
| 100° C. | 4.3 | 51 | 90.5 | 16.3 |
| VI | 136 | 323 | 351 | 437 |

{1} ASTM method for kinematic vis is D445
{2} ASTM method for VI is D2270
{3} The results for the pure fractions were calculated using this logarithmic blending rule: Ln (Blend Viscosity) = x1 * ln (viscosity1) + x2 * ln (viscosity2) where x = weight fraction of each component viscosity = kinematic viscosity of each component In this equation, the viscosity of the blend {labeled functionalized Di-45 with ester can be measured directly. The properties of the free ester can be measured on a fully esterified product which would be produced separately. The weight fraction of the free ester can be determined by either gas chromatography or thermal gravimetric analyses (TGA) and the amount of functionalized ester can be determined by difference. As a result, all values in the equation are known except viscosity 2 (the viscosity of the functionalized ester) which can then be determined by direct substitution.

Selected silicone-containing esters derived from this group were evaluated for their dispersion properties. The solid selected for dispersion was a zinc oxide product coated with triethyl caprylyl silane known commercially as Z-Cote HP1, manufactured and sold by BASF. It is a potent sunscreen product used in concentrations of about 2 to about 10% usually in oil-in-water formulations. The test utilized to measure the dispersion effectiveness of a molecule is as follows:

Test pigments/particulates are thoroughly dispersed using a Silverson Mixer at 9000 rpm in 15 gram increments in the selected emollient.

After each addition the Brookfield viscosity at ambient temperature was determined.

Additions of 15 grams are continued until the viscosity increases substantially; usually 10 to 100-fold (approximately 10,000 cP+).

The test significance is as follows:

Evaluates the wetting efficiency of an emollient.

The lower the dispersion viscosity increase compared to the emollient's neat viscosity, the better the wetting of the pigment.

Low viscosity increase is associated with good wetting, i.e., uniform spreading of the emollient, little or no air entrainment, and no agglomeration (i.e., small particle size).

High viscosity increase is associated with agglomeration.

An arbitrary rating system has been established to compare the efficacy and is shown graphically in FIG. 1 along with the data generated for the silicone esters in FIGS. 2 and 3.

The data set forth in FIGS. 2 and 3 clearly demonstrate that the addition of the silicone moieties in Exxon Di-10, Di-45, Di-100 and Exxon D2 and D10 results in substantially improved dispersion properties versus the non-silicone products MCP 2262 and PureSyn 3E20. Additionally, substantial improvement over the polyalphaolefin PureSyn 6 is observed. It is anticipated that the advantage associated with these results translates into excellent potential for use of these silicone products in sunscreen, antiperspirant/deodorant and facial makeup formulations at lower concentrations, i.e., 1% to 15%, because of their superior dispersing properties.

The tables below demonstrate the unique refractive index, surface tension and viscosity properties of the use of the silicone esters of the present disclosure versus conventional PAO's, etc.

TABLE 1

| Property | Ester | PAO | Exxon Di-45 | Exxon D10 | Silicone |
|---|---|---|---|---|---|
| Refractive Index @25° C. | 1.45 | 1.45 | 1.43 | 1.44 | 1.40 |
| Surface Tension @25° C., dynes/cm | 30 | 29-31 | 22.3 | 22.7 | 21.2 |
| Viscosity @25° C., cSt | 34 | 900 | 170 | 290 | 500 |

TABLE 2

| | Wt % Ester | SpectraSyn4 | SpectraSyn 40 | GR II EHC 45 | Dow 200-5 cSt | Dow 200-200 cSt |
|---|---|---|---|---|---|---|
| C8C10 TMP | 100 | S | S | S | H | H |
| Exxon Di-10 | <2 | S | Vsl H | S | S | H |
| Exxon Di-45 | <2 | S | S | S | S | H |
| Exxon Di-100 | <2 | Vls H | H | S | S | Vsl H |
| Exxon D2 | <2 | S | S | S | I | H |
| Exxon D10 | <2 | S | S | S | S | H |

In Table 1 two silicone esters (i.e., Exxon Di-45 and Exxon D10) were compared to an ester, a polyalphaolefin, and a silicone, wherein the following properties were compared:

1. Refractive Index: Ester addition to Silicone backbone will increase refractive index from 1.40 to Ester and PAO range. This is greatly beneficial in personal care formulation, since increase in even the 2nd decimal number is significant.

2. Surface Tension: Silicone is known for its characteristic surface tension to be used in the formulation. Ester and PAO can hardly compete. It is shown here that by addition of an ester on a silicone backbone, the silicone ester of the present disclosure, will have the same great surface tension character as silicone, but with added compatibility benefit with other fluids that silicone alone is lacking.

3. Viscosity: As a reference on thickness of the fluids.

Table 2 shows the beneficial compatibility of silicone ester fluids with other typical reference fluids, which is unique and can be tailored by molecular design. ~10 wt % fluid in left column is mixed with reference fluids on the top row for solubility test.

C8C10TMP is the ester attached to the silicone backbone (in left column along with other silicone ester fluids containing greater than 2% C8C10TMP ester). SpectraSyn 4 is a low viscosity short chain polyalphaolefin hydrocarbon. SpectraSyn 40 is a high viscosity long chain polyalphaolefin hydrocarbon. Gr II EHC 45 is a typical mineral oil hydrocarbon. Dow 200-5 cSt—is a low viscosity short chain silicone fluid. Dow 200-200 cSt—is a high viscosity long chain silicone fluid.

Typically, organic fluids are not soluble in silicone fluids. This table 2 shows the following:

Addition of an ester on a silicone backbone can change its compatibility with all hydrocarbons;

The same silicone ester molecule can be compatible with silicone fluids; and

Compatibility can be tailored by tailoring the molecule by dictating the silicone backbone and the ester type and ratio.

Formulations

1. 2-in-1 Shampoo with Silicone Esters

Description:

This 2-in-1 shampoo provides luxurious and lubricious foam while delivering excellent cleaning and conditioning without residual buildup.

| Phase | Ingredient | INCI Designation | Wt % |
|---|---|---|---|
| A | Deionized Water | Water | 53.04 |
| A | Disodium EDTA | Disodium EDTA | 0.20 |
| A | Carbopol Ultrez 20 | Carbomer | 0.30 |
| A | Mackadet APB | Commercial Package from McIntyre | 45.00 |
| B | Silicone Ester | | 1.00 |
| C | Belle Aire Tango Mango 23008 | Fragrance | 0.05 |
| D | Kathon CG | Methylchloroisothiazolinone (and) Methylisothiazolinone | 0.05 |
| E | NaOH (20% Soln.) | Sodium Hydroxide | 0.00 |
| E | Citric Acid (20% Soln.) | Citric Acid | 0.00 |
| F | Sodium Chloride | Sodium Chloride | 0.11 |
| | Total | | 100.00 |

Blending Procedure

1. Dissolve Disodium EDTA in water and add Mackadet APB, heat to 60° C.
2. Mix phase B and heat to 60° C. and mix until uniform
3. Add phase B to phase C and cool to 40° C., Add phase E to the A Batch
4. Add phase D
5. Adjust pH to 6.5-7.0 with phase E
6. Adjust viscosity to 6,000-12,000 cP with ammonium chloride solution

2. Medicated Lip Balm with Silicone Esters

| Phase | Ingredient | INCI Designation | Wt % |
|---|---|---|---|
| A | Ultrapure Petrolatum | Petrolatum | 93.30 |
| A | Silicone Esters | | 3.00 |
| B | Camphor | Camphor | 2.50 |
| C | Menthol | Menthol | 0.50 |
| D | Flavor MF 102079 | Flavor | 0.50 |
| E | Vitamin E Acetate | Tocopheryl Acetate | 0.10 |
| F | D&C Green # 6 (0.1% in oil) | Green 6 | 0.10 |
| | Total | | 100.00 |

Blending Procedure

1. Heat phase A to 70° C.
2. Cool to 60° C. and add remaining ingredients.
3. Pour at 55° C.

3. Moisturizing Lotion with Silicone Ester

| Phase | Ingredient | INCI Designation | Wt % |
|---|---|---|---|
| A | Deionized Water | Water | 62.80 |
| A | Carbopol 980 (2% Soln) | Carbomer | 20.00 |
| A | Na$_2$EDTA | Disodium EDTA | 0.10 |
| A | Propylene Glycol | Propylene Glycol | 2.00 |
| B | Promulgen D | Cetearyl Alcohol (and) Ceteareth-20 | 2.00 |
| B | Silicone Ester | | 10.00 |
| B | Arlacel 165 | Glyceryl Stearate (and) PEG-100 Stearate | 1.50 |
| C | Triethanolamine 99% to pH 6.5-7.0 | Triethanolamine | 0.60 |
| D | Germaben II | Propylene Glycol (and) Diazolidinyl Urea (and) Methylparaben (and) Propylparaben | 1.00 |
| | Total | | 100.00 |

Blending Procedure

1. Heat phase A to 70° C.
2. Heat phase B to 70° C.
3. Add phase B to phase A
4. Add phase C. Cool to 50° C. and add phase D.

4. Organic Sunscreen Spray with PureSyn 2,4, and Silicone Esters

Description:

PureSyn 2, 4, silicone esters are used in this ~SPF 30 spray that has a broad spectrum UVA/UVB protection. The combination of a fast, a medium spreading PureSyn plus a slow spreading silicone ester product provides an improved elegant cascading emollient feel.

| Phase | Ingredient | INCI Designation | Wt % |
|---|---|---|---|
| A | Ceralution C | Water (and) Caprylic/Capric Triglyceride (and) Glycerin (and) Ceteareth-25 (and) Sodium Dicocoylethylenediamine PEG-15 Sulfate (and) Sodium Lauroyl Lactylate (and) Behenyl Alcohol (and) Glyceryl Stearate Citrate (and) Xanthan Gum | 12.00 |
| B | Finsolv TN | C12-15 Alkyl Benzoate | 3.50 |

-continued

| Phase | Ingredient | INCI Designation | Wt % |
|---|---|---|---|
| B | Mandorwax | Hydrogenated Sweet Almond Oil (and) Hydrogenated Sweet Almond Oil Unsaponifiables (and) Prunus Amygdalus Dulcis (Sweet Almond) Oil Unsaponifiables | 0.50 |
| B | Uvinul MC 80 | Ethylhexyl Methoxycinnamate (Octinoxate) | 7.50 |
| B | Uvinul M 40 | Benzophenone-3 (Oxybenzone) | 5.00 |
| B | PureSyn 2 | Hydrogenated C6-14 Olefin Polymers | 1.00 |
| B | PureSyn 4 | Hydrogenated C6-14 Olefin Polymers | 1.00 |
| B | Silicone Ester | | 1.00 |
| B | Dow Corning 245 Fluid | Cyclopentasiloxane | 1.00 |
| B | Escalol 587 | Ethylhexyl Salicylate (Octisalate) | 5.00 |
| B | Vitamin E Acetate | Tocopheryl Acetate | 0.10 |
| B | Uvinul N 539 T | Octocrylene | 9.00 |
| C | Deionized Water | Water (Aqua) | 49.80 |
| C | LaraCare A200 | Galactoarabinan | 2.00 |
| C | Avicel PC-611 | Microcrystalline Cellulose (and) Cellulose Gum | 0.50 |
| C | Disodium EDTA | Disodium EDTA | 0.10 |
| C | Germaben II | Propylene Glycol (and) Diazolidinyl Urea (and) Methyl Paraben (and) Propylparaben | 1.00 |
| | Total | | 100.00 |

Blending Procedure:

1. Add phase A to a beaker large enough to accommodate the entire batch, heat with mixing to 85° C.

2. In a separate vessel combine phase B ingredients and heat to 85° C. with mixing. Very slowly add phase B to phase A with rapid mixing maintaining 85° C. Homogenize for 3 minutes at 4,500-5,000 rpm.

3. Heat the phase C water to 50° C. and disperse the Laracare A200 into the water and mix well. Disperse the Avicel PC-611 into the water as well and mix until hydrated (batch will become uniform in consistency, minimum time=10 minutes). Add Disodium EDTA to this mixture and mix for an additional 15 minutes. Add this premixed phase C to the batch with mixing.

4. Cool entire batch to 40° C. to room temperature, Add phase D to the batch with mixing. homogenize for 2 minutes at 5,000 rpm and package.

5. Antiperspirant Roll-on with Silicone Esters

ANTIPERSPIRANT ROLL-ON with Silicone Esters

| Phase | Ingredient | INCI Designation | A Wt % | B Wt % | C Wt % | D Wt % |
|---|---|---|---|---|---|---|
| A | DC 345 Fluid | Cyclomethicone | 51.2 | 31.2 | 26.2 | 16.2 |
| A | Bentone Bel VS-5 PC | Cyclomethicone (and) Quaternium-18 Hectorite (and) Propylene Carbonate | 12.5 | 12.5 | 12.5 | 12.5 |
| B | Silicone Ester | | 10.0 | 30.0 | 35.0 | 45.0 |
| C | Rezal 36GP | Aluminum Zirconium Tetrachlorohydrex-GLY | 20.0 | 20.0 | 20.0 | 20.0 |

-continued

ANTIPERSPIRANT ROLL-ON with Silicone Esters

| Phase | Ingredient | INCI Designation | A Wt % | B Wt % | C Wt % | D Wt % |
|---|---|---|---|---|---|---|
| C | Talc 127 | Talc | 2.0 | 2.0 | 2.0 | 2.0 |
| D | Dow Corning 190 Surfactant | PPG/PEG-18/18 Dimethicone | 4.0 | 4.0 | 4.0 | 4.0 |
| D | Fragrance | Fragrance | 0.3 | 0.3 | 0.3 | 0.3 |
| | Total | | 100.0 | 100.0 | 100.0 | 100.0 |

Blending Procedure

1. Using the Silverson at 3000 rpm with large head mix phase A (3 min.)

2. Add phases B & C

3. Mix phase D together and add to batch

4. Mix on Silverson until uniform

REDUCED RESIDUE ANTIPERSPIRANT STICK with Silicone Esters

| Phase | Ingredient | INCI Designation | A Wt % | B Wt % | C Wt % |
|---|---|---|---|---|---|
| A | Silicone Ester | | 10.0 | 25.0 | 53.5 |
| A | Hydrogenated Castor Oil | Hydrogenated Castor Oil | 2.5 | 2.5 | 2.5 |
| A | PEG-8 Distearate | PEG-8 Distearate | 1.0 | 1.0 | 1.0 |
| A | Stearyl Alcohol | Stearyl Alcohol | 18.0 | 18.0 | 18.0 |
| B | Dow Corning 345 Fluid | Cyclomethicone | 43.5 | 28.5 | |
| C | Cabosil M-5 | Silica | 0.5 | 0.5 | 0.5 |
| D | REACH AZP 908 SUF | Aluminum Zirconium Tetrachlorohydrex GLY | 24.0 | 24.0 | 24.0 |
| E | Fragrance | Fragrance | 0.5 | 0.5 | 0.5 |
| | Total | | 100.0 | 100.0 | 100.0 |

Blending Procedure

1. Mix and heat ingredients of phase A to 85° C. or until clear, Cool to 70° C.

2. Heat phase B to 70° C., add to phase A and mix well (except Formulation C)

3. Slowly add phases C and D while maintaining 70° C.

4. Mix well until homogeneous, cool to 56-58° C. and add phase E

5. Mix well and pour into stick containers

6. Reduced Residue Antiperspirant Stick with Silicone Esters

REDUCED RESIDUE ANTIPERSPIRANT STICK with Silicone Esters

| Phase | Ingredient | INCI Designation | A Wt % | B Wt % | C |
|---|---|---|---|---|---|
| A | Silicone Ester | | 20.0 | 10.0 | 5 |
| A | Hydrogenated | Hydrogenated Castor Oil | 2.5 | 2.5 | 2.5 |
| A | PEG-8 Distearate | PEG-8 Distearate | 1.0 | 1.0 | 1.0 |
| A | Stearyl Alcohol | Stearyl Alcohol | 18.0 | 18.0 | 18.0 |
| B | Dow Corning 345 Fluid | Cyclomethicone | 33.5 | 43.5 | 48.5 |
| C | Cabosil M-5 | Silica | 0.5 | 0.5 | 0.5 |

-continued

REDUCED RESIDUE ANTIPERSPIRANT STICK
with Silicone Esters

| Phase | Ingredient | INCI Designation | A Wt % | B Wt % | C |
|---|---|---|---|---|---|
| D | REACH AZP 908 SUF | Aluminum Zirconium Tetrachlorohydrex GLY | 24.0 | 24.0 | 24.0 |
| E | Fragrance | Fragrance | 0.5 | 0.5 | 0.5 |
|   | Total |   | 100.0 | 100.0 | 100.0 |

Blending Procedure

1. Mix and heat ingredients of phase A to 85° C. or until clear, Cool to 70° C.

2. Heat phase B to 70° C., add to phase A and mix well (except Formulation C)

3 Slowly add phases C and D while maintaining 70° C.

4. Mix well until homogeneous, cool to 56-58° C. and add phase E

5. Mix well and pour into stick containers

The present disclosure has been described with particular reference to the preferred embodiments. It should be understood that the foregoing descriptions and examples are only illustrative of the invention. Various alternatives and modifications thereof can be devised by those skilled in the art without departing from the spirit and scope of the present disclosure. Accordingly, the present disclosure is intended to embrace all such alternatives, modifications, and variations that fall within the scope of the appended claims.

What is claimed is:

1. A cosmetic composition comprising: (a) an aqueous phase comprising: (i) water, and (ii) at least one cosmetically active ingredient; (b) a coupling agent; and (c) an oil phase comprising: (i) an isoparaffin solvent, and (ii) a silicone-containing solvent having the formula:

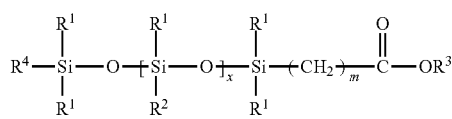

wherein:

R$^1$ are independently selected from the group consisting of: an alkyl having 1-5 carbon atoms, a substituted alkyl having 1-5 carbon atoms optionally substituted by one or more fluorine atoms, and a phenyl, and R$^2$ is selected from the group consisting of: hydrogen, alkyl of 1 to 45 carbon atoms, substituted alkyl of 1 to 45 carbon atoms optionally substituted by one or more fluorine atoms, an aryl, a partially esterified ester-containing group represented by the formula:

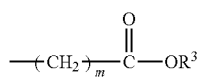

a reverse ester thereof represented by the formula:

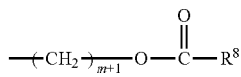

the formula:

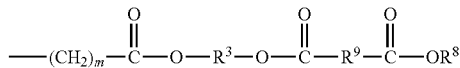

and a reverse ester thereof represented by the formula:

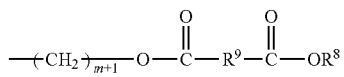

provided that if R$^1$ is anything but methyl or ethyl, then R$^2$ must be a methyl, ethyl or butyl, R$^3$ is derived from a partially esterified ester residue;

R$^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

R$^9$ is selected from the group consisting of: an arylene, an alkylene of 1 to 22 carbon atoms, substituted alkylene of 1 to 22 carbon atoms optionally substituted by one or more fluorine atoms and arylene;

R$^4$ is selected from the group consisting of: alkyl of 1 to 45 carbon atoms, substituted alkyl of 1 to 45 carbon atoms optionally substituted by one or more fluorine atoms, aryl, said ester-containing group and said compound derived from reverse esters thereof;

m is an integer between about 5 to about 22; and x is an integer between about 0 to about 1000;

wherein said composition has at least 1 compound derived from said partially esterified ester-containing group or said reverse ester thereof.

2. The composition according to claim 1, wherein said isoparaffin solvent has a boiling range between about 100 to 340° C., wherein said isoparaffin constitutes between about 1 to 75% by weight, of the total of said oil phase.

3. The composition according to claim 1, further comprising (d) a silicone-containing surfactant.

4. The composition according to claim 3, wherein said silicone-containing surfactant is an alkoxylated, alkyl substituted siloxane surface active agent.

5. The composition according to claim 4, wherein said silicone-containing surfactant is dimethicone copolyol or a mixture of dimethicone copolyol and cyclomethicone.

6. The composition according to claim 3, wherein said silicone-containing surfactant is present in an amount between about 0.2 to 2% by weight, of the total weight of said composition.

7. The composition according to claim 1, wherein said coupling agent is present in an amount between about 10 to 30% by weight, of the total weight of said composition.

8. The composition according to claim 1, wherein said isoparaffin solvent is a saturated aliphatic hydrocarbon containing at least one side chain, and wherein the total carbon atoms are in the range between about 8 to 20.

9. The composition according to claim 1, wherein said isoparaffin constitutes between about 25 to 50% by weight, of the total of said oil phase.

10. The composition according to claim 1, further comprising at least one additional additive selected from the group consisting of: emollients, humectants, antiseptics, antioxidants, chelating agents, ultraviolet absorbers, colorants, fragrances and preservatives.

11. The composition according to claim 1, wherein said composition is a deodorant, antiperspirant, sunscreen, insect repellent or anti-fungal agent.

12. The composition according to claim 1, wherein said composition is one selected from the group consisting of: sunscreens, shampoos, lip balms, moisturizing lotions, and antiperspirants.

13. The composition according to claim 1, wherein said composition exhibits at least one property selected from the group consisting of:
   substantially odor-free;
   a refractive index in the range between about 1.41 to about 1.46;
   solubility parameters in the range between about 7 to about 9 +/−1.5 'd(i) @ 25° C. (cal/cc)$^{1/2}$;
   viscosity in the range between about 35 to about 2450 cSt @ 25° C.; and
surface tension in the range between about 20 to about 23 dynes/cm.

* * * * *